United States Patent [19]

Azuma et al.

[11] Patent Number: 4,880,616

[45] Date of Patent: Nov. 14, 1989

[54] STABLE STANNOUS CHLORIDE COMPOSITION FOR LABELING WITH RADIOACTIVE TECHNETIUM

[75] Inventors: Makoto Azuma; Jun Takahashi, both of Hyogo; Hirohiko Yamauchi, Osaka; Nobuo Ueda, Hyogo, all of Japan

[73] Assignee: Nihon Medi-Physics Co., Ltd, Hyogo, Japan

[21] Appl. No.: 135,527

[22] Filed: Dec. 17, 1987

Related U.S. Application Data

[63] Continuation of Ser. No. 791,474, Oct. 25, 1985, abandoned.

[30] Foreign Application Priority Data

Oct. 26, 1984 [JP] Japan .................................. 59-226395

[51] Int. Cl.$^4$ ............................................ A61K 49/02
[52] U.S. Cl. .................................................... 424/1.1
[58] Field of Search .......................... 424/1.1, 9, 131; 534/14; 423/494; 422/61

[56] References Cited

U.S. PATENT DOCUMENTS

| | | | |
|---|---|---|---|
| 3,812,264 | 5/1974 | Nouel | 424/1.1 |
| 3,863,004 | 1/1975 | Wolfangel | 424/1.1 |
| 3,875,299 | 4/1975 | Winchell et al. | 424/1.1 |
| 3,968,221 | 7/1976 | Winchell et al. | 424/1.1 |
| 4,071,613 | 1/1978 | Hunter, Jr. | 424/1.1 |
| 4,075,314 | 2/1978 | Wolfangel et al. | 424/1.1 |
| 4,082,840 | 4/1978 | Adler et al. | 424/1.1 |
| 4,087,516 | 5/1978 | Laidler et al. | 424/1.1 |
| 4,226,846 | 10/1980 | Saklad | 424/1.1 |
| 4,291,012 | 9/1981 | Streckler et al. | 424/1.1 |
| 4,293,537 | 10/1981 | Wong | 424/1.1 |
| 4,364,920 | 12/1982 | Winchell | 424/1.1 |
| 4,439,413 | 3/1984 | Hagashi et al. | 424/1.1 |
| 4,454,107 | 6/1984 | Rolleston | 424/1.1 |
| 4,500,507 | 2/1985 | Wong | 424/1.1 |
| 4,645,659 | 2/1987 | Harrison | 424/1.1 |
| 4,692,324 | 1/1984 | Davis | 424/1.1 |

OTHER PUBLICATIONS

The Merck Index, pp. 978-979, 8th Ed. (1968).
Patel et al., Journal of Nuclear Medicine, vol. 20 (8), pp. 877-881 (1979).
Mellor, Comprehensive Treatise on Inorg. and Theor. Chemistry, vol. 7, pp. 424-435, (1927).
The Merck Index, pp. 978-979, 8th Ed., (1968).
Kato, M., Journal of Nuclear Medicine, vol. 20, pp. 1071-1074 (1979).
Chemical Abstracts 97: 133547h (1982).

*Primary Examiner*—John F. Terapane
*Assistant Examiner*—J. E. Thomas

[57] ABSTRACT

A non-radioactive labeling composition for preparation of a technetium 99m-labeled radioactive diagnostic agent, which comprises a small amount of a lyophilized product obtained from a stannous chloride solution having a high concentration of stannous chloride charged in a container.

2 Claims, No Drawings

STABLE STANNOUS CHLORIDE COMPOSITION FOR LABELING WITH RADIOACTIVE TECHNETIUM

This application is a continuation of application Ser. No. 06/791474, filed Oct. 25, 1985, now abandoned.

The present invention relates to a stable stannous chloride composition for labeling with radioactive technetium. More particularly, it relates to a stable and less toxic, non-radioactive labeling composition useful for preparation of a radioactive technetium-labeled tin colloid for liver scintigraphy or for preparation of radioactive technetium-labeled red blood cells in a human body.

Since technetium-99m ($^{99m}$Tc) emits only gamma-rays of about 140 KeV without beta-rays and has a short half life (i.e. about 6 hours), it is quite suitable as a nuclide to be introduced into human bodies for diagnosis. Because of this reason, its utilization in the field of nuclear medicine has rapidly developed and expanded in recent years.

Among various $^{99m}$Tc-labeled radioactive medicines as recently developed, there are included those which are used for scintigraphic visualization of the form or shape of a liver by utilization of the phenomenon that a certain kind of colloid particles is taken intoi the Kupffer cells of the liver. Particularly, the $^{99m}$Tc-labeled tin colloid as reported in 1972 (Winchell et al.: Journal of Nuclear Medicine, 13, 58 (1972)) is widely used, like $^{99m}$Tc-labeled sulfur colloid and $^{99m}$Tc-labeled calcium phytate colloid, on clinic as an excellent liver imaging agent.

For preparation of the $^{99m}$Tc-labeled tin colloid, there is usually adopted a process wherein a non-radioactive labeling composition comprising stannous ion (i.e. divalent tin ion) and a physiological saline solution (e.g. 0.9% by weight NaCl) comprising sodium pertechnetate are mixed together. In order to carry out this process, it is necessary to use a stable and less toxic non-radioactive labeling composition comprising stannous ion, which can form $^{99m}$Tc-labeled tin colloids having such a particle size and a particle concentration as being capable of affording an excellent liver scintigram when administered intravenously into a human body. As such non-radioactive labeling composition, there is commonly used a dilute aqueous solution of stannous chloride (0.5 to 2.0 mmol/liter) as reported in said Winchell et al. literature. However, the stannous chloride in this dilute aqueous solution is apt to be hydrolyzed or oxidized with air, and a great problem is present on the stability and the storage manner. For stabilization of a composition unstable in the solution state, lyophilization is often adopted, but there has not been reported any lyophilized stannous chloride composition for preparation of the $^{99}$mTc-labeled tin colloid. In fact, a dilute aqueous solution of stannous chloride is seriously hydrolyzed or oxidized during the operation of lyophilization.

Some attempts have been made in order to solve the problems as above mentioned. One of them is to use stannous fluoride and sodium fluoride in place of stannous chloride on the preparation of a non-radioactive labeling composition comprising stannous ion (Japanese Patent Publication (examined) No. 15089/82). In general, however, a fluoride species is highly toxic in comparison with the corresponding chloride so that said attempt is not an ideal solution.

As a result of the extensive study, it has now been found that a stable and less toxic, non-radioactive labeling composition for preparation of a $^{99m}$Tc-labeled tin colloid which can afford an excellent liver scintigram is obtainable by the use of a lyophilized product of a high concentration stannous chloride solution prepared by charging a small quantity of said solution into a container and subjecting the content of the container to lyophilization. The present invention is based on the above finding and thus provides a stable and less toxic, non-radioactive labeling composition.

Radioactive medicines which can be retained in the blood circulation system without being taken by any organ or tissue when administered into a blood vessel are useful for the observation of a heart blood pool, a brain blood vessel, a peripheral blood vessel, etc. and the collection of diagnostic information. Those medicines as heretofore reported include $^{99m}$Tc-labeled human serum albumin ($^{99m}$Tc-HSA) and $^{99m}$Tc-labeled red blood cells ($^{99m}$Tc-RBC). However, $^{99m}$Tc-HSA has a great problem in labeling efficiency and stability in a human body. $^{99m}$Tc-RBC of which the labeling is effected outside a human body requires a troublesome operation for its preparation. In addition, there is a possibility of infection with microorganisms during the operation. Due to these reasons, they are not broadly used.

An attempt has been made on labeling of red blood cells with $^{99m}$Tc in a human body. According to this attempt, a solution containing stannous ion in the form of phosphate chelate is administered into a blood vessel, and then a pertechnetate ($^{99m}$TcO$_4^-$) is administered so as to label red blood cells with $^{99m}$Tc specifically. Since the operation is simple, the labeling efficiency is high and the stability after labeling is sufficient, the above labeling procedure is adopted widely. As the phosphate chelate of stannous ion in this labeling procedure, there are used tin-pyrophosphate (Sn-PPi), tin-ethane-1-hydroxy-1,1-diphosphonate (Sn-EHDP), tin-methylenediphosphonate (Sn-MDP), etc. The phosphate chelating compound to be used in combination with tin, i.e. stannous ion, plays a role of prevention of stannous ion in the non-radioactive labeling composition from hydrolysis and oxidation with air for stabilization. If a sufficiently stable non-radioactive labeling composition can be prepared by the use of stannous chloride alone without using the phosphate chelating compound, it is of course much favorable. It has now been found that said non-radioactive labeling composition of the invention which is prepared by the use of stannous chloride alone is also useful for labeling of red blood cells with $^{99m}$Tc in a human body.

The non-radioactive labeling composition of the invention can be prepared from a solution of stannous chloride, made utilizing anhydrous stannous chloride (SnCl$_2$) or stannous chloride hydrate (usually SnCl$_2$.2H$_2$O).

The solvent to be used for preparation of the stannous chloride solution may be any one which can afford a designed concentration of stannous chloride and does not prevent the resulting stannous chloride solution from lyophilization. The most preferred one is water. Insofar as lyophilization is not prevented, any solvent mixture such as water-methanol, water-ethanol or water-dimethylsulfoxide may be employed.

Preparation of the stannous chloride solution is to be effected in an atmosphere of inert gas such as nitrogen or argon in order to avoid hydrolysis or oxidation.

Likewise, the solvent to be used for preparation of the stannous chloride solution is to be kept free from oxygen by removal of dissolved oxygen with said inert gas.

Every constant quantity of the stannous chloride solution as thus prepared is charged to a container such as a vial or an ampoule, preferably under the atmosphere of an inert gas as above exemplified.

Lyophilization may be effected by a per se conventional procedure, i.e. cooling the stannous chloride solution first to freeze and removing the solvent from the frozen stannous chloride solution under reduced pressure by sublimation. In order to avoid the separating out of stannous chloride or the solate of stannous chloride in the lyophilization step or the disuniformalization of the stannous chloride concentration in the lyophilized product, it is preferred to cool the stannous chloride solution as quickly as possible for accomplishment of the freezing.

After completion of the lyophilization, the lyophilized product is stored in a sealed state in vacuo or in an inert gas atmosphere for avoiding the oxidation.

The concentration of the stannous chloride solution prior to the lyophilization is to be not less than 0.05 mol/liter, to be not more than the solubility of stannous chloride in the used solvent at room temperature and not to cause the separating out of stannous chloride or its solvate by completion of freezing in the freezing step of the lyophilization. The preferred concentration is from about 0.5 to 2.0 mol/liter. Even when the solubility of stannous chloride in the used solvent is lower than the stannous chloride concentration on its preparation as the result of the lowering of the temperature in the freezing step, the invention process is workable if the separating out of stannous chloride or its solvate does not take place before completion of the freezing by maintaining the stannous chloride solution in a supersaturated state.

The quantity of the stannous chloride solution to be charged into each of the containers such as vials or ampoules is to be determined by how many persons are to be tested by the use of each container comprising the non-radioactive labeling composition. Taking the risk of air oxidation and microbil infection into consideration, each container is preferred to contain a sufficient amount of the non-radioactive labeling composition to test from one to five persons. Inclusion of such a large amount as sufficient to test 10 persons or more in each container as presently and commonly adopted is to be avoided. Thus, each container is favored to contain the non-radioactive labeling composition for preparation of a $^{99m}$Tc-labeled tin colloid in an amount of about 0.5 micromol to 5.0 micromol of stannous chloride. When the concentration of the stannous chloride solution is 1.0 mol/liter, the charging quantity in each container may be from 0.5 microliter to 5.0 microliters.

In the case of the non-radioactive labeling composition being to be used for labeling red blood cells with $^{99m}$Tc in a human body, each container is preferred to contain the non-radioactive labeling composition in an amount of about 10.0 micromol to 100.0 micromol of stannous chloride. When the concentration of the stannous chloride solution is 1.0 mol/liter, the charging quantity in each container may be from 10.0 microliters to 100.0 microliters.

For labeling of red blood cells with $^{99m}$Tc in a human body by the use of the non-radioactive labeling composition according to this invention, a preferred dose of stannous ion to be administered is from about 10 micrograms to 20 micrograms (i.e. from 0.0842 micromol to 0.168 micromol) (corresponding to stannous chloride of 15.97 micrograms to 31.95 micrograms) per kilogram of bodyweight.

On the use of the non-radioactive labeling composition of the invention for preparation of the $^{99m}$Tc-labeled tin colloid, sterilized, pyrogen-free, dissolved oxygen-free water is added to a container comprising the non-radioactive labeling composition in an amount of 1 milliliter per 1 micromol of stannous chloride present in the container to dissolve the same. A same quantity of a physiological saline solution containing $^{99m}$Tc in the pertechnetate form as that of water is added thereto. The resultant mixture is allowed to stand at room temperature for about 15 minutes to give $^{99m}$Tc-labeled tin colloid. The radioactivity of $^{99m}$Tc as used may be determined by how many persons are to be tested by each container comprising the $^{99m}$Tc-labeled tin colloid. Usually, the dose of $^{99m}$Tc to be administered for static livver scintigraphy with $^{99m}$Tc-labeled tin colloid is from about 1 mCi to 5 mCi per each person. After the intravenous administration, photographing is effected by the use of a gamma camera or a scintillation scanner to obtain a liver scintigram.

On the use of the non-radioactive labeling composition of the invention for labeling red blood cells in a human body, sterilized, pyrogen-free, dissolved oxygen-free water is added to a container comprising the non-radioactive labeling composition in an amount of 1 milliliter per 5 micromol of stannous chloride present in the container to dissolve the same. The quantity of the resultant solution is adjusted so as to make 20 micrograms of stannous ion (corresponding to 32 micrograms of stannous chloride) per kg of the bodyweight of a person to be tested, and then the resulting solution is administered to the person intravenously. After 30 minutes, a physiological saline solution containing $^{99m}$Tc in the sodium pertechnetate form is intravenously administered to said person, whereby the labeling of the red blood cells with $^{99m}$Tc in the body of said person can be attained. The radioactivity of $^{99m}$Tc as administered may be determined based on the purpose of testing, the function of gamma camera, etc. The dose of $^{99m}$Tc to be administered usually for labeling of red blood cells in cardiac nuclear medicine is from about 5 mCi to 30 mCi per each person.

In this invention, the most characteristic feature resides in the use of a stannous chloride solution of relatively high concentration. Most of the non-radioactive labeling compositions for labeling with $^{99m}$Tc (i.e. the kit-type radioactive medicines for labeling with $^{99m}$Tc) which are presently available on the market are lyophilized preparations comprising stannic ion as the reducing agent for $^{99m}$Tc, and the amount of stannous chloride therein is usually several micromols per each container. The successful lyophilization of the composition comprising such a small amount of stannous chloride as above avoiding the hydrolysis and oxidation of stannous ion can be achieved only by the co-existence of a compound to be labeled, a stabilizer, a carrier, etc. which may protect stannous ion from hydrolyzing and oxidizing. In other words, it was a common knowledge that the lyophilization of a solution solely containing stannous chloride without hydrolysis or oxidation is extremely difficult, and in fact, any non-radioactive labeling composition comprising stannous chloride alone has never practically been proposed.

According to this invention, a stannous chloride solution of relatively high concentration is subjected to lyophilization by a procedure as hereinabove explained so that a non-radioactive labeling composition comprising stannous chloride can be produced without any material hydrolysis or oxidation of stannous ion. The concentration of the stannous chloride solution to be subjected to lyophilization may be not less than 0.1 mol/liter in general but should not exceed the saturated concentration of stannous chloride under the operation condition. The amount of such stannous chloride solution to be charged into each container is normally not more than 500 microliters.

Practical and presently preferred embodiments of the invention are illustratively shown in the following Examples.

EXAMPLE 1

Manufacture of a non-radioactive labeling composition for preparation of $^{99m}$Tc-labeled tin colloid (hereinafter referred to as "FDSn-COL"):

Into sterilized pyrogen-free water, germ-free nitrogen gas was introduced to eliminate oxygen dissolved therein. All the subsequent operations were carried out under the sterilized condition in nitrogen stream. In the oxygen-free water (100 ml), anhydrous stannous chloride (18.961 g; 0.1 mol) was dissolved. Under nitrogen stream, each 3.0 μl of this stannous chloride solution (concentration, 1.0 mol/liter) was charged through a filter having a pore size of 0.22 μm into a vial of which the interior was substituted with nitrogen stream and subjected to lyophilization by the aid of a lyophilizer. Thereafter, the pressure was elevated to the atmospheric pressure by introduction of nitrogen therein, and the vial was sealed with a rubber cork under nitrogen stream to obtain the non-radioactive labeling composition "FDSn-COL".

EXAMPLE 2

Manufacture of a $^{99m}$Tc-labeled tin colloid (hereinafter referred to as "Tc-(FDSn-COL)") by the use of "FDSn-COL":

"FDSn-COL" as manufactured in Example 1 was dissolved in sterilized water (3.0 ml) containing no pyrogen substance and eliminating oxygen. The resultant solution was admixed with a physiologically saline solution containing $^{99m}$Tc (5 mCi) in the form of sodium pertechnetate (3.0 ml) and stirred well, followed by allowing to stand at room temperature for 30 minutes to obtain the $^{99m}$Tc-labeled tin colloid, i.e. "Tc-(FDSn-COL)".

EXAMPLE 3

Property of "Tc-(FDSn-COL)"

(A) "Tc-(FDSn-COL)" as prepared in Example 2 was subjected to thin layer chromatography using a silica gel thin layer plate and methyl ethyl ketone as a developing solvent. Scanning with a radiochromatoscanner revealed the presence of a single spot having radioactivity at Rf=0.00, and any other radioactive peak was not recognized.

In the above chromatography system, $^{99m}$Tc in the form of pertechnetate is to be developed to Rf=0.95 to 1.00, and the $^{99m}$Tc-labeled tin colloid is to be retained at the original point. Therefore, the presence of a single radioactive spot at Rf=0.00 may mean that the labeling efficiency is 100%.

(B) "Tc-(FDSn-COL)" (0.2 ml) was intravenously administered to each of S.D. (Sprague-Dawley) strain female rats. Fifteen minutes and thirty minutes after the administration, the animals were sacrificed, and various organs were taken out and subjected to measurement of radioactivity.

For comparison, a $^{99m}$Tc labeled radioactive composition was prepared by the use of a stannous chloride solution of low concentration. Namely, a non-radioactive labeling composition was manufactured in the same manner as in Example 1 but using a stannous chloride solution having a concentration of 2 mmol/liter and charging the stannous chloride solution into a vial in an amount of 1.5 ml. With the resultant non-radioactive labeling composition, the operation was carried out in the same manner as in Example 2 to give a $^{99m}$Tc-labeled tin colloid (hereinafte referred to as "Tc-(FDSn-REF)"). By the use of "Tc-(FDSn-REF)", the same animal test as above was effected.

The results are shown in Table 1.

TABLE 1

Distribution of "Tc-(FDSn-COL)" and "Tc-(FDSn-REF)" in organs of rats (% of radioactivity administered; average in 5 animals)

| Organs | 15 minutes | | 30 minutes | |
|---|---|---|---|---|
| | A | B | A | B |
| Liver | 95.76 | 67.38 | 95.26 | 64.98 |
| Spleen | 2.54 | 4.05 | 2.88 | 5.23 |
| Lung | 0.90 | 9.65 | 0.85 | 10.73 |
| Remaining | 0.82 | 18.93 | 1.02 | 19.06 |

Note:
A: "Tc-(FDSn-COL)";
B: "Tc-(FDSn-REF)".

From the above results, it is understood that the "Tc-(FDSn-COL)" has an excellent distributing ability as a radioactive diagnostic agent for liver scintigraphy. Namely, "Tc-(FDSn-COL)" shows such a high level of accumulation in liver as not less than 95%, while "Tc-(FDSn-REF)" shows a lower accumulation in liver with a higher accumulation in other organs.

EXAMPLE 4

Stability of "FDSn-COL"

"FDSn-COL" as prepared in Example 1 was stored at a temperature of 3° to 6° C. in the absence of light for a period of 100 or 200 days. By the use of the resulting "FDSn-COL", "Tc-(FDSn-COL)" was prepared as in Example 2. As in Example 3, the labeling efficiency and the distribution in organs were examined. The labeling efficiency was 100% after the storage of 100 days or 200 days. The distribution in the organs of rats was as shown in Table 2 wherein the values indicate those 15 minutes after the administration.

TABLE 2

Distribution of "Tc-(FDSn-COL)" in organs of rats (% to radioactivity administered; average in 5 animals)

| Organs | 100 Days after preparation | 200 Days after prepartion |
|---|---|---|
| Liver | 95.88 | 95.26 |
| Spleen | 2.25 | 2.74 |
| Lung | 0.97 | 0.90 |
| Remaining | 0.91 | 1.14 |

From the above results, it is understood that "FDSn-COL" is stable at a temperature of 3° to 6° C. for a period of not less than 200 days.

EXAMPLE 5

Stability of "Tc-(FDSn-COL)"

"Tc-(FDSn-COL)" as prepared in Example 2 was stored at room temperature in the absence of light for 3 or 6 hours. As in Example 3, the distribution in the organs of rats was examined. The results are shown in Table 3 wherein the values indicate those 15 minutes after the administration.

TABLE 3

Distribution of "Tc-(FDSn-COL)" in organs of rats (% to radioactivity administered; average in 5 animals)

| Organs | Three hours after preparation | Six hours after prepartion |
|---|---|---|
| Liver | 95.84 | 95.01 |
| Spleen | 2.05 | 2.68 |
| Lung | 1.00 | 1.23 |
| Remaining | 1.12 | 1.09 |

From the above results, it is understood that "Tc-(FDSn-COL)" is stable over a period of not less than 6 hours.

EXAMPLE 6

Manufacture of a non-radioactive labeling composition for labeling of red blood cells (hereinafter referred to as "FDSn-RBC"):

In the same manner as in Example 1 but charging 20.0 µl of the stannous chloride solution into a vial, there was prepared a non-radioactive labeling composition for labeling of red blood cells, i.e. "FDSn-RBC".

EXAMPLE 7

Labeling of red blood cells with $^{99m}$Tc by the use of "FDSn-RBC" in rats:

"FDSn-RBC" as prepared in Example 6 was dissolved in sterilized oxygen-free water (10.0 ml) containing no pyrogen substance. The resultant solution was adjusted so as to make a dose of stannous ion in an amount of 20 µg per kg of bodyweight and then administered to each of S.D. (Sprague-Dawley) strain female rats (bodyweight, 145–180 g) through a tail vein. Thirty minutes after the administration, a physiological saline solution (0.25 ml) containing $^{99m}$Tc (0.5 mCi) in the form of sodium pertechnetate was administered through a tail vein at the opposite side. After the lapse of a certain period of time, the animals were subjected to abdominal incision, and blood (5–7 ml) was collected from the aorta with a heparinized syringe. A part of the collected blood (1.0 ml) was put into a vial for radioactive determination with a pipet and counted on a gamma counter. By comparing the determined value thus obtained with that of a separately prepared standard sample, the percentage of $^{99m}$Tc present in 1 ml of blood (after corrected with decrement) to the whole injected dose was calculated. This value was indicated as %ID/ml Blood (ID=injected dose). For comparison of the data obtained in animals having different bodyweights, this value was then normalized to an average body weight of 160 g according to the following equation:

%ID/ml Blood (norm)=[%/ml Blood]× $W$/160 wherein W is a bodyweight of rat (g).

The remaining blood (3 to 5 ml) was centrifuged (800 g, 20 min) to be separated into plasma and blood cells. After centrifugation, the hematocrit value (volume percent of blood cells in blood, %/Hct) was obtained. A part of the separated plasma (1.0 ml) was placed into a vial for radioactive determination with a pipet. The plasma (1.0 ml) and the above mentioned blood (1.0 ml) were counted in the same geometrical position (the same count efficiency position) in the gamma counter, and from the determined values, the background values were subtracted to obtain net count values per 1 minute, C(plasma) and C(blood). From these values, the percentages of radioactivity distribution in the red blood cells and in the plasma (%/RBC and %/Plasma), respectively) were calculated according to the following equation:

$$\%/\text{Plasma} = \frac{C(\text{Plasma}) \times (1 - \%/\text{Hct}/100)}{C(\text{Blood})} \times 100$$

%/RBD = 100 − (%/Plasma)

wherein RBC is the abbreviation of red blood cells.

Then, the percentage of radioactivity present in 1 ml of red blood cells to the whole dose of radioactivity [% ID/ml RBC (norm)] was calculated according to the following equation:

% ID/ml RBC (norm)=[%/ml Blood (norm)]×[%/RBC]/[%/Hct]

Finally, the percentage of radioactivity present in the whole red blood cells to the whole dose of radioactivity (%ID in whole RBC) was calculated according to the following equation, on the assumption that the whole amount of blood (ml) was 6.5% of the bodyweight (g):

%ID in whole RBC

= [%ID/ml Blood) × W × (6.5/100) × [(%/RBC)/100]

= [ID/ml Blood (norm)] × 160 (6.5/100) × [(%/RBC)/100]

Using the experimental procedure described above, the following evaluations were performed, of which the results are shown in Table 4.

TABLE 4

| Time(*) (hr) | Intracorporeal $^{99m}$Tc-labeling with FDSn-RBC (average in 5 animals) | | | | |
|---|---|---|---|---|---|
| | A | B | C | D | E |
| 1 | 9.43 | 98.93 | 1.07 | 20.69 | 98.59 |
| 2 | 9.50 | 98.56 | 1.44 | 19.89 | 97.38 |

Note:
(*)Time lapsed after administration of $^{99m}$Tc pertechnetate until collection of blood;
A: % ID/ml Blood (norm);
B: %/RBC;
C: %/Plasma;
D: % ID/ml RBC (norm);
E: % ID in whole RBC With the amount of Sn(II) of 20 ug/kg of the bodyweight, as mentioned in Example 8 below, the efficiency of labeling of red blood cells reached the maximum in each of the labeling compositions. As understood from Table 4, all of the labeling compositions of the invention showed a labeling efficiency of 95% or more in the % ID in whole RBC even after 1 or 2 hours after the administration.

EXAMPLE 8

Relationship between the dose of "FDSn-RBC" and the efficiency of intracorporeal labeling of red blood cells:

In the same manner as in Example 7 but changing the dose of Sn(II), i.e. 1, 5, 10, 20 or 40 μg/1 kg of the bodyweight, the labeling efficiency of "FDSn-RBC" was observed. The results are shown in Table 5, in which the collection of blood was effected 1 hour after the administration.

TABLE 5

| Dose of Sn(II) (ug/kg) | Intracorporeal $^{99m}$Tc-labeling with "FDSn-RBC" (average in 5 animals) | | | | |
|---|---|---|---|---|---|
| | A | B | C | D | E |
| 1 | 1.12 | 39.28 | 40.72 | 0.88 | 4.57 |
| 5 | 6.57 | 97.56 | 1.73 | 15.46 | 66.66 |
| 10 | 9.53 | 99.05 | 0.95 | 20.65 | 98.17 |
| 20 | 9.55 | 98.97 | 1.03 | 20.71 | 98.30 |
| 40 | 8.42 | 98.02 | 1.98 | 17.82 | 85.83 |

Note:
A: % ID/ml Blood (norm);
B: %/RBC;
C: %/Plasma;
D: % ID/ml RBC (norm);
E: % ID in whole RBC As apparent from this Table, administration of 10 to 20 μg/kg of Sn(II) in the form of "FDSn-RBC" attains a high yield of red blood cell labeling.

It was shown by these experiments that intracorporeal labeling of red blood cells with $^{99m}$Tc could be realized with extreme simplicity by the use of the labeling agents according to the invention.

EXAMPLE 9

Stability of "FDSn-RBC" for labeling

"FDSn-RBC" as obtained in Example 6 was stored at 3° to 6° C. in the absence of from light for 100 or 200 days. By the use of the resulting labeling agents, the intracorporeal labeling of red blood cells with $^{99m}$Tc was effected as in Example 7. The results are shown in Table 6, in which the collection of blood was effected 1 hour after the administration.

TABLE 6

| Storage time (day) | Intracorporeal $^{99m}$Tc-labeling with "FDSn-RBC" (average in 5 animals) | | | | |
|---|---|---|---|---|---|
| | A | B | C | D | E |
| 100 | 9.39 | 98.90 | 1.10 | 19.99 | 96.58 |
| 200 | 9.41 | 98.95 | 1.02 | 20.32 | 96.83 |

Note:
(*)A: % ID/ml Blood (norm);
B: %/RBC;
C: %/Plasma;
D: % ID/ml RBC (norm);
E: % ID in whole RBC As apparent from this Table, the labeling efficiency of "FDSn-RBC" of red blood cell is stable even after 200 days after the preparation.

EXAMPLE 10

Toxicity of the non-radioactive labeling composition according to the invention:

Since the non-radioactive labeling composition of the invention comprises lyophilized stannous chloride alone in the cases for preparation of $^{99m}$Tc labeled tin colloid and for labeling of red blood cells, its toxicity is substantially equal to stannous chloride itself.

In this Example, the acute toxicity with intravenous administration of the non-radioactive labeling composition to rats or mice was evaluated. Namely, sterilized, pyrogen-free and oxygen-free water (1.0 ml) was added to a vial containing "FDSn-RBC" to make a stannous chloride solution (20 μmol/ml, 3.792 μg/ml). The resultant solution was intravenously administered to male and female ICR strain mice and S.D. strain rats. After 14 days, the accumulative death percentage was determined, and the lethal dose 50 (LD$_{50}$) was calculated by the Litchfield-Wilcoxon's method. As the result, the LD$_{50}$ value of stannous chloride was 28±3 mg/kg and 33±3 mg/kg respectively in female mice and male mice, and 17±2 mg/kg and 18±3 mg/kg respectively in female rats and male rats.

The dose of the non-radioactive labeling composition to human beings may be 9.48 μg/kg (with the assumption that a total amount of one vial of FDSn-COL is administered to a person of 60 kilograms in bodyweight) as stannous chloride at the maximum in case of using for preparation of $^{99m}$Tc-labeled tin colloid, and 31.95 μg/kg (corresponding to 20 μg/kg of stannous ion) in case of using for labeling of red blood cells in a human body. When these doses are compared with the LD$_{50}$ values of female rats which are considered to be the most sensitivve among the tested animals, said dose is about 1/1790 that of the LD$_{50}$ value in case of preparation of $^{99m}$Tc-labeled tin colloid and about 1/530 that of the LD$_{50}$ value in case of labeling of red blood cells in a human being.

From the above results, it may be said that the non-radioactive labeling composition of the invention can be administered intravenously into human beings with sufficient safety. The safety of the non-radioactive labeling composition according to the invention may be also supported by the fact that stannous chloride is widely and clinically administered to human beings with or without chelating agents.

What is claimed is:

1. A process for preparing a technetium 99m-labeled radioactive diagnostic agent consisting essentially of the steps of:
   (a) preparing a solution of stannous chloride in a concentration of not less than 1.0 mol/liter by dissolving stannous chloride alone in water,
   (b) charging solution prepared in step (a) to a container in an amount of not more than 500 microliters,
   (c) lyophilizing to provide stannous chloride in a dry solid state in said container,
   (d) adding water to said container to dissolve the stannous chloride therein and admixing $^{99m}$Tc in the pertechnetate form to form $^{99m}$Tc-labeled tin colloid.

2. The diagnostic agent prepared by the method of claim 1.

* * * * *